United States Patent [19]

Daniel et al.

[11] 4,409,835

[45] Oct. 18, 1983

[54] DUMMY CHEST LOAD DISTRIBUTION TRANSDUCER

[75] Inventors: Roger P. Daniel, Dearborn; Carl D. Yost, Ann Arbor, both of Mich.

[73] Assignee: Ford Motor Company, Dearborn, Mich.

[21] Appl. No.: 289,017

[22] Filed: Jul. 31, 1981

[51] Int. Cl.³ ............................................. G01N 33/00
[52] U.S. Cl. ............................... 73/432 R; 73/862.04; 434/274
[58] Field of Search ............... 73/432 J, 432 SD, 172, 73/862.04; 434/274; 364/578

[56] References Cited

U.S. PATENT DOCUMENTS

| | | | |
|---|---|---|---|
| 3,757,431 | 9/1973 | Daniel | 434/274 |
| 3,841,163 | 10/1974 | Daniel | 73/432 J |
| 4,261,113 | 4/1981 | Alderson | 73/432 J X |

FOREIGN PATENT DOCUMENTS

| | | | |
|---|---|---|---|
| 2358716 | 3/1978 | France | 73/432 J |
| 2452752 | 11/1980 | France | 73/432 J |

*Primary Examiner*—Anthony V. Ciarlante
*Assistant Examiner*—Joseph W. Roskos
*Attorney, Agent, or Firm*—Daniel M. Stock; John J. Roethel; Clifford L. Sadler

[57] ABSTRACT

A chest transducer for measuring the gross load distribution and direction of loading on the thorax of an anthropomorphic dummy during dynamic testing of a vehicle passenger restraint system. The chest transducer comprises a simulated rib cage constructed and arranged to permit dynamic measurements of at least three components of restraint system loads applied to a plurality of key segments of the rib cage during restraint system testing.

5 Claims, 4 Drawing Figures

DUMMY CHEST LOAD DISTRIBUTION TRANSDUCER

BACKGROUND OF THE INVENTION

In 1975, a report was presented at the 19th Stapp Car Crash Conference by personnel from the Technical University of Berlin describing the possibility of concentrated lower rib cage loading from a belt restraint system. A second report presented at the 1977 Stapp Conference expanded on the subject. No evidence was available, however, that such concentrated loading was occurring in most highway accidents, although rib fracture was known to occur in severe highway crashes, particularly with older occupants.

During developmental tests conducted by personnel of the assignee of the present application on one proposal for an experimental passive restraint system early in 1979, strain gages were applied to several dummy ribs to permit a comparison of the strain distribution on the dummy chest when restrained by the experimental system and by a production belt system. Significant differences were noted in this test program in the dummy rib strain gage measurements. Although the strain gaged ribs did demonstrate that differences were present, they could not provide actual load data to measure the magnitude of loading on different parts of the rib cage for the following reasons.

1. The dummy rib cage used was a poor representation of the skeletal shape of the human rib cage.
2. Once a rib was stressed beyond its yield point, the data could not be quantified and the rib transducer was ruined.
3. Without elaborate instrumentation techniques, different chest loading patterns tended to distort or even cancel out the strain measurements of interest. Thus, the reliability of such measurements tended to be low.
4. Because of the possible complicated load patterns on the ribs, it became apparent it would be very difficult to ever obtain a vectored load reading in pounds at an angle of application.

To better understand these complicated load patterns, a transducer is required that is capable of accurately measuring the gross load distribution and direction of loading over a dummy rib cage during a restraint system test. By using such a transducer, it is possible to quantify the effect of restraint system variables on chest loading patterns.

Design constraints for the proposed transducer comprise a rib cage simulation that:

1. Has the approximate size and shape of a partly compressed human rib cage;
2. Completely isolates the forces into the lower rib cage from those applied to the rest of the chest;
3. Provides triaxial load measurement in at least four key locations on the rib cage;
4. Provides sufficient chest deflection properties to stabilize the belt location on the chest;
5. Utilizes the head, neck, arms and lower torso of currently available or future dummies;
6. Has essentially the same weight and weight distribution of a nontransducer dummy chest;
7. Accommodates for frontal (+30°) impacts only; and
8. Is durable, reliable and easy to use.

SUMMARY OF THE INVENTION

This invention relates to a chest transducer for dynamically measuring the gross load distribution and direction of loading of a vehicle passenger restraint system on the thorax of an anthropomorphic dummy. The chest transducer comprises a simulated rib cage supported on a thoracic spine box of the anthropomorphic dummy. The simulated rib cage approximates the size and shape of a human rib cage and is constructed and arranged to isolate forces applied to the lower rib cage structure from those applied to the remainder of the thorax. The rib cage is covered by a padding of firm load-deflection properties capable of simulating compression of the frontal wall of the chest by torso belt components of the belt restraint system. Multi-directional load measuring cells are mounted on the thoracic spine box and coupled in a plurality of key supportive locations to the rib cage to sense forces applied to the latter.

DESCRIPTION OF THE DRAWINGS

Futuer features and advantages of the present invention will be made more apparent as this description proceeds, reference being had to the accompanying drawings, wherein.

DETAILED DESCRIPTION OF THE INVENTION

Figure 1:
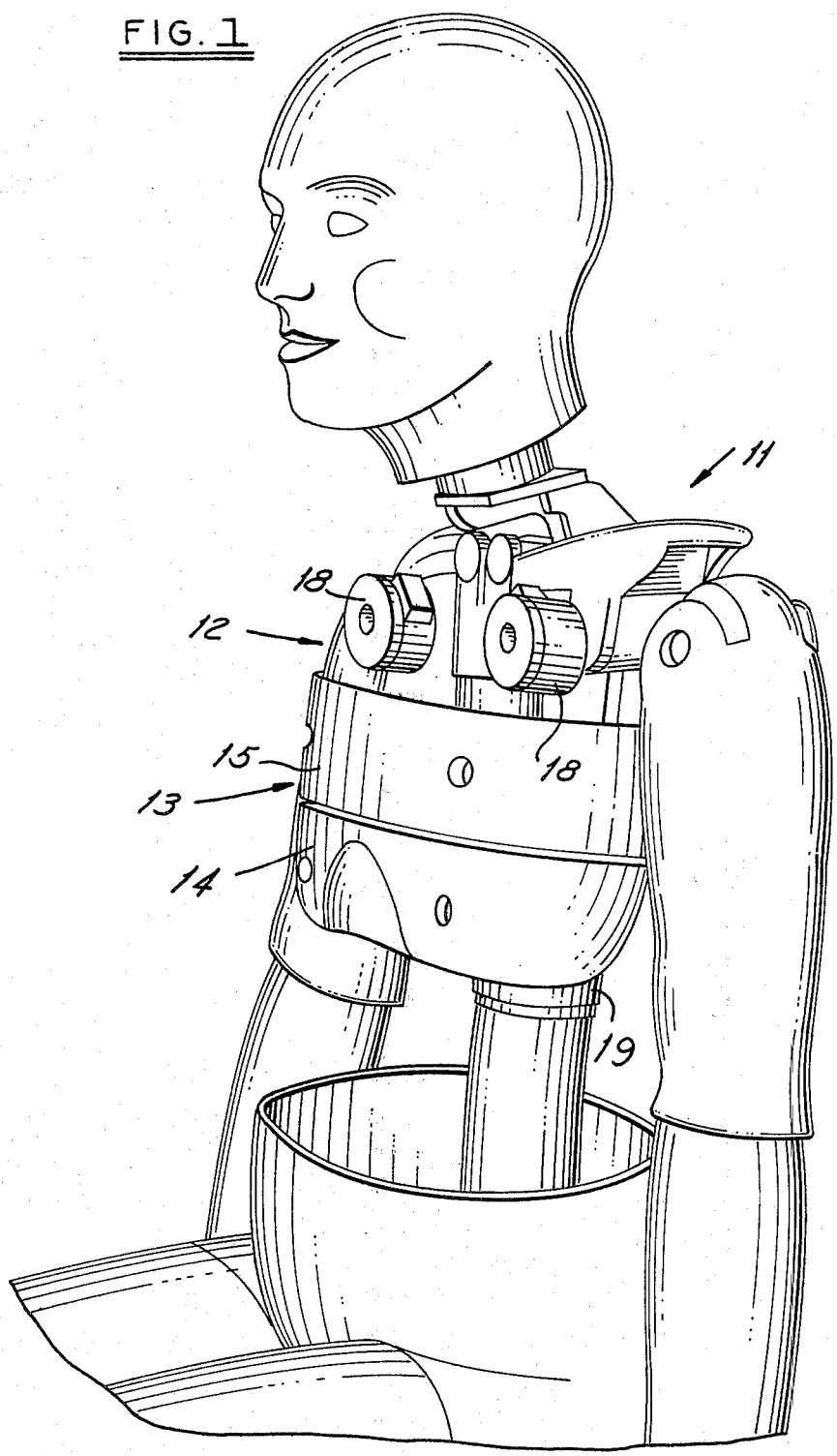
FIG. 1 is a perspective view of a partially assembled anthropomorphic dummy having a chest transducer embodying the present invention.
Figure 2:
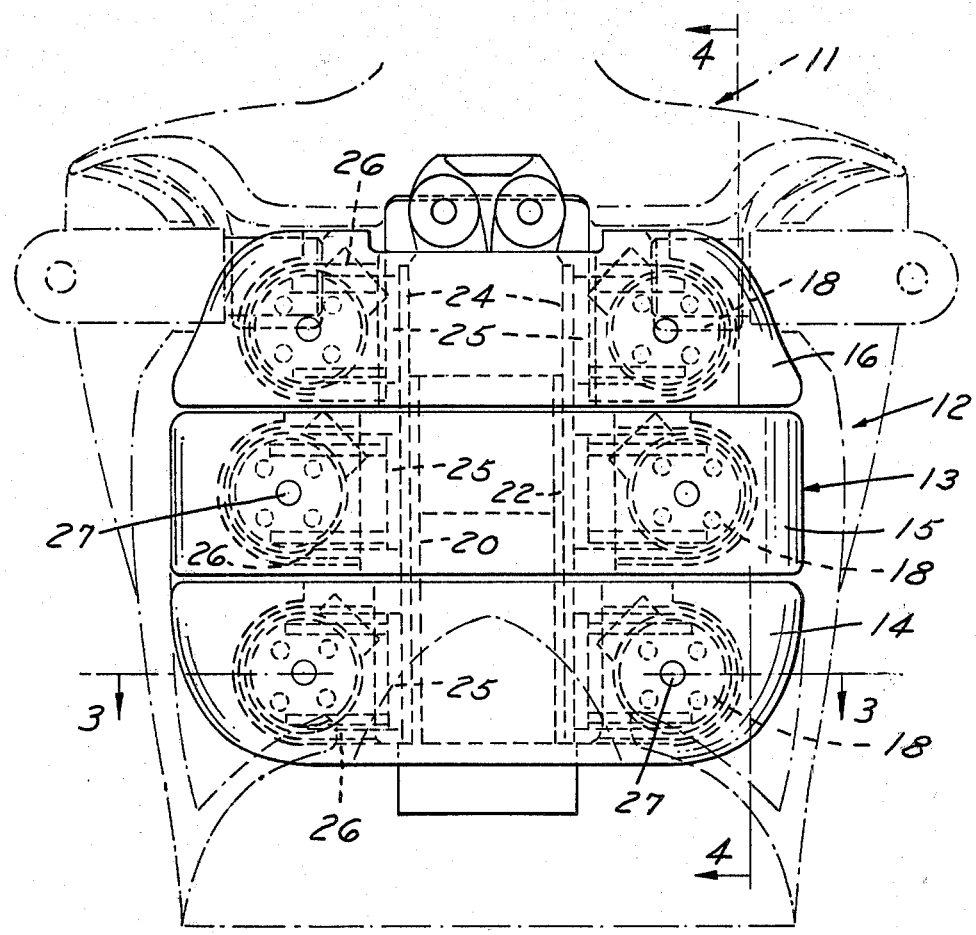
FIG. 2 is a frontal elevation of the thorax of the anthropomorphic dummy of FIG. 1.

Referring now to the drawings, FIG. 1 represents a partially assembled male dummy 11 having a modified thorax to accommodate a chest transducer 12 in accordance with the present invention. As used herein, the dummy thorax corresponds to that part of the body of a man between the neck and the abdomen.

The chest transducer 12 is formed as a simulated rib cage 13 that comprises a plurality of vertically stacked, mutually isolated beams 14, 15 and 16 that extend across the frontal width of the thorax and are shaped to represent a partially compressed rib cage. The beams preferably are cast of lightweight metal and are machined to eliminate as much weight as possible without unduly weakening them, see FIG. 3.

Figure 3:
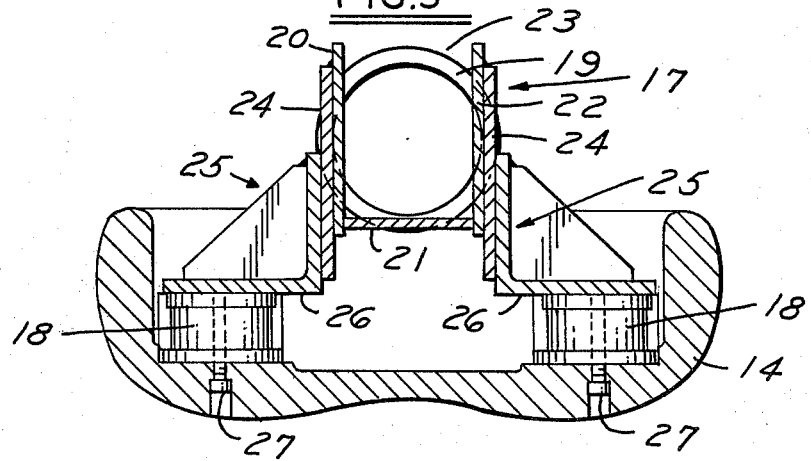
FIG. 3 is a section view taken on the line 3—3 of FIG. 2.

The beams 14, 15 and 16 are mounted to a dummy thoracic spine box 17 through triaxial load cells 18. As best seen in FIG. 3, a typical dummy spine, as shown in the drawings, comprises a tubular column 19 partially encompassed by a box formed of three elongated plates 20, 21 and 22, the box being opened on its fourth side, the side facing to the rear of the dummy thorax. Reinforcing plates 24 are welded to the side walls 20 and 22 of the box. These plates 24 support right angle brackets 25, with the laterally extending leg 26 of each bracket providing a base for a triaxial load cell 18 mounted thereon by suitable fasteners. Each beam 14, 15 and 16 is bolted adjacent each of it ends by a bolt 27 to a triaxial load cell 18.

The triaxial load cells 18 are black box items as far as this invention is concerned. For this reason, the internal details of the load cells are not shown or described. For the prototype chest transducer, the load cell specifications were as follows:

2024 Aluminum case
2.0 inch diameter
1.25 inch in height
1800 lb. axial ($F_z$) load capacity
1000 lb. each for vertical ($F_y$) and lateral ($F_x$) loads
Overload capacity—50%.

Figure 4:
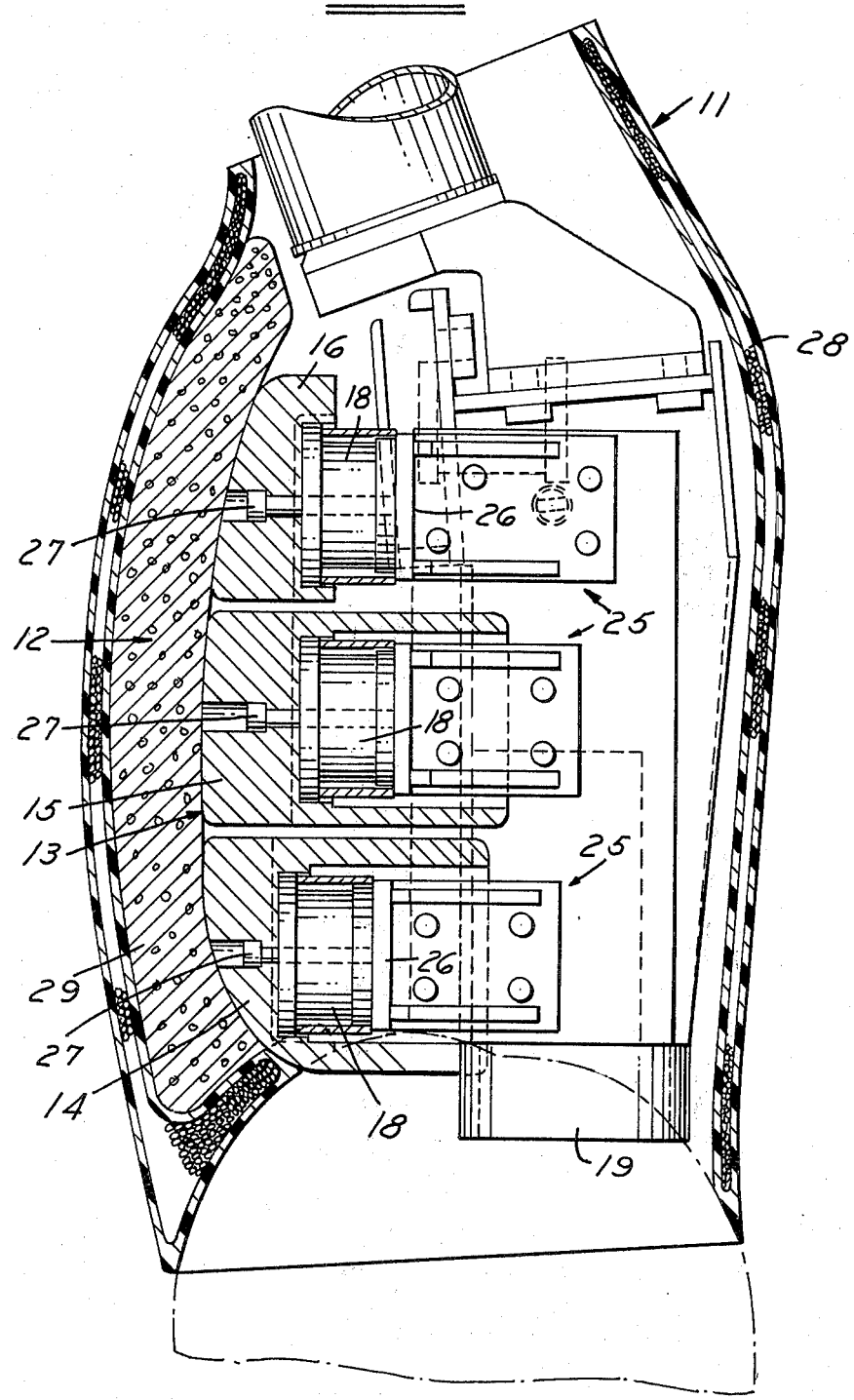
FIG. 4 is a section view taken on the line 4—4 of FIG. 2.

As best seen in FIG. 4, the chest transducer 12 is concealed from view within the test dummy. The thorax of the dummy in completed form has an outer jacket 28 which may be of a suitable self-skinning foam material. A one inch layer of a foam type plastic 29 (about 8 psi, 25% compression load), beneath the outer jacket 28, covers the load beams to give a "compressionability" to the chest and to pocket a torso or shoulder harness belt (not shown) in a somewhat humanlike manner.

In an initial experimental use of the chest transducer, two essentially identical 30 mph Hyge sled tests were conducted. The purpose was to ascertain whether the loading patterns postulated by the 1975 and 1977 Stapp Conference reports could be measured. The experimental conditions were judged conducive to the type of torso movement that could produce these loads. The first of the reports described the possibility of concentrated lower rib cage loading from a upper torso belt restraint system. The second report expanded on the subject, but no evidence was available that such concentrated loading was occurring in most highway accidents, although rib fracture was known to occur in severe highway crashes, particularly with older occupants.

The two tests were conducted with the dummy occupying the right front passenger seat, which would bring the torso strap diagonally down across the chest from the right shoulder toward the left hip. In both tests, the most significant loads were taken in the right (outboard) upper region of the chest and in the lower left region of the chest. The upper area of the chest is judged to be very strong, and the load applied to that region should not be a major concern. The load is primarily in the anterior/posterior (a-p) direction. The lower area of the rib cage is judged to be comparatively weak, but it had to sustain very significant upward, lateral and a-p loads—closely matching the postulated dummy and actual cadaver results of the 1975 and 1977 Stapp Conference reports. In both tests, chest acceleration was well within a 60 G-3 ms limit. The values were 38 and 42 G-3 ms.

Human tolerance data for various portions of the human chest are very limited; hence there are no absolute tolerance values with which to compare the load data obtained with this chest transducer embodying the present invention. There have many many years of experience, however, with three-point restraint systems in millions of vehicles on the highway, as well as with a closely studied two-point/knee bolster system in common use on some motor vehicles. Sled tests with such systems could provide comparative data and could lead to empirical guidelines with which to compare experimental restraint systems.

It is to be understood that this invention is not limited to the exact construction illustrated and described above, but that various changes and modifications may be made without departing from the spirit and scope of the invention as defined in the appended claims.

We claim:

1. A chest transducer for measuring the gross load distribution and direction of loading of a vehicle passenger restraint system on the thorax of an anthropomorphic dummy;

the chest transducer comprising:

a simulated rib cage supported on a simulated thoracic spine of the anthropomorphic dummy;

the simulated rib cage approximating the size and shape of a human rib cage and being constructed and arranged to isolate forces applied to the lower rib cage structure from those applied to the remainder of the thorax;

a padding of firm load-deflection properties capable of simulating compression of the frontal wall of the chest by components of the vehicle passenger restraint system;

and multi-directional load measurement cells mounted on the simulated thoracic spine and coupled in a plurality of key supportive locations to the rib cage to sense the forces applied to the latter.

2. A chest transducer according to claim 1, in which:

the simulated rib cage comprises a plurality of vertically stacked, mutually isolated beams that extend across the frontal width of the thorax and are shaped to represent a partially compressed rib cage.

3. A chest transducer according to claim 2, in which:

the load cells are positioned at each end of selected ones of the beams.

4. A chest transducer according to claim 2, in which:

the beams forming the rib cage are three in number;

a load cell is positioned contiguously to each beam end whereby the vector direction and magnitude of the load can be measured at six sectors of the rib cage during dynamic testing of a vehicle passenger restraint system.

5. A chest transducer according to claims 1, 2 or 4, in which:

the loads have triaxial measuring capabilities for measuring inward, vertical up and down and lateral loads on the rib cage.

* * * * *